United States Patent [19]

Fahrni et al.

[11] Patent Number: 5,041,563

[45] Date of Patent: Aug. 20, 1991

[54] REARRANGEMENT PROCESS

[75] Inventors: Peter Fahrni, Füllinsdorf; Theodor Siegfried, Basel, both of Switzerland

[73] Assignee: Hoffman-La Roche Inc., Nutley, N.J.

[21] Appl. No.: 529,683

[22] Filed: May 22, 1990

Related U.S. Application Data

[63] Continuation of Ser. No. 345,043, Apr. 28, 1989, abandoned, which is a continuation of Ser. No. 910,581, Sep. 23, 1986, abandoned, which is a continuation of Ser. No. 706,053, Feb. 27, 1985, abandoned, which is a continuation of Ser. No. 462,261, Jan. 31, 1983, abandoned.

[30] Foreign Application Priority Data

Feb. 12, 1982 [CH] Switzerland ............................ 891/82
Dec. 10, 1982 [CH] Switzerland .......................... 7218/82

[51] Int. Cl.$^5$ ............................................ C07D 307/32
[52] U.S. Cl. ................................. 549/315; 549/316; 564/394; 564/438
[58] Field of Search ................ 549/315, 316; 564/394, 564/438

[56] References Cited

U.S. PATENT DOCUMENTS

| 2,443,487 | 6/1948 | Wenner | 549/315 |
| 4,275,234 | 6/1981 | Baniel et al. | 562/584 |
| 4,489,209 | 12/1984 | Chang | 564/438 |

FOREIGN PATENT DOCUMENTS 892446 10/1953 Fed. Rep. of Germany.

OTHER PUBLICATIONS

Arthur and Elizabeth Rose, "The Condensed Chemical Dictionary", p. 87, 7th ed., 1966, Reinhold Pub. Corp. N. Y.
CRC 53rd. pp. D-120 and D-121.
Hackh's Chemical Dictionary, 4th Ed., p. 526 (1969).
Chem. Abst., 52,4203d (1956).

Primary Examiner—C. Warren Ivy
Assistant Examiner—Ba K. Trinh
Attorney, Agent, or Firm—George M. Gould; George W. Johnston; Alan P. Kass

[57] ABSTRACT

A process for the manufacture of ascorbic acid from 2-ketogulonic acid esters (KGAE) utilizing amine salts of the latter is disclosed.

10 Claims, No Drawings

REARRANGEMENT PROCESS

This application is a continuation of application Ser. No. 07/345,043, filed Apr. 28, 1989, now abandoned; which is a continuation of Ser. No. 06/910,581, filed Sept. 23, 1986, now abandoned; which is a continuation of Ser. No. 06/706,053, filed Feb. 27, 1985, now abandoned; which is a continuation of Ser. No. 06/462,261, filed Jan. 31, 1983, now abandoned.

DESCRIPTION OF THE INVENTION

The present invention is concerned with a novel process for the manufacture of ascorbic acid from 2-ketogulonic acid esters (KGAE).

Ketogulonic acid or its esters, which occur in the penultimate step in conventional ascorbic acid syntheses, must be rearranged to ascorbic acid. In this rearrangement, which can be carried out under acidic or alkaline conditions, certain problems always arise. Thus, on the one hand, in the case of the acidic rearrangement the problem consists especially in that the yields obtainable are not satisfactory and the quality of the ascorbic acid obtained leaves much to be desired. Moreover, the reaction times in the case of the acidic rearrangement are in general very long.

On the other hand, in the case of the alkaline rearrangement, the problem consists essentially in that the bases used for the rearrangement form salts with the ascorbic acid, which, for the purpose of isolating the pure ascorbic acid, must be further cleaved as a rule by the addition of an acid. This cleavage again results in salts from which the ascorbic acid can be separated only with difficulty and which cannot be used further, at least to some extent.

There accordingly exists a need for a process in accordance with which ascorbic acid can be obtained in a simple manner from ketogulonic acid esters and in good yield and in which the base required for the rearrangement can be recovered readily and can be re-used in the process.

The aforementioned problems can now be eliminated by means of the process provided by the present invention. In other words, it has been found that when certain amines are used in the rearrangement of KGAE the aforementioned problems do not occur.

The process provided by the present invention accordingly comprises reacting a ketogulonic acid ester of the general formula

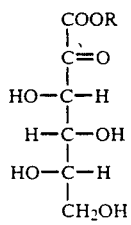

I wherein R signifies lower alkyl, with an amine containing 12 to 38 carbon atoms in a suitable organic solvent and cleaving the resulting ascorbic acid amine salt of the general formula

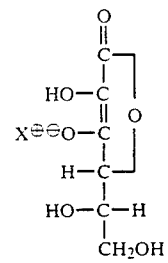

II wherein $X^\oplus$ represents the ammonium ion of the amine used, without neutralization and isolating the ascorbic acid as well as, if desired, the amine used.

The term "lower alkyl" signifies in the scope of the present invention alkyl groups containing 1 to 5 carbon atoms such as methyl, ethyl, propyl, isopropyl, butyl and the like. Alkyl groups containing 1 to 3 carbon atoms and especially methyl and ethyl are preferred.

As amines there come into consideration in the scope of the present invention primary, secondary and tertiary amines containing 12 to 38 carbon atoms. The lower limit of the carbon number is determined, inter alia, by the solubility in the organic solvent used for the cleavage of the ascorbic acid amine salt of formula II. The upper limit of the carbon atom number is, on the other hand, determined by the solubility in the solvent used for the reaction between the KGAE and the amine.

The amines which can be used are preferred in the following sequence;

Tertiary amines > secondary amines > primary amines.

Primary amines include not only straight-chain but also branched-chain amines, with the branched-chain amines being preferred. Especially preferred are, moreover, those containing 12 to 24 carbon atoms. Moreover, under primary amines there are to be understood certain liquid, basic ion exchangers such as, for example Primene JMT or Amberlite LA-3.

Secondary amines include not only straight-chain but also branched-chain alkylamines as well as aromatic amines. Preferred secondary amines are branched-chain alkylamines and especially those containing 16 to 25 carbon atoms. Dibenzylamine is the preferred aromatic secondary amine. Moreover, under secondary amines there are to be understood certain liquid, basic ion exchangers such as, for example, Amberlite LA-1 or Amberlite LA-2.

Tertiary amines include especially straight-chain and partially branched-chain aliphatic amines, the straight-chain alkylamines and especially those containing 15 to 30 carbon atoms being preferred.

The secondary amines and the tertiary amines can contain the same alkyl chains or different alkyl chains.

The following are examples of amines and preferred amines which can be used in the present invention.
Primene JMT,
Amberlite LA-3,
α-amino-diphenylmethane,
1,2-diphenylethylamine,
bis(2-ethylhexyl)amine,
Amberlite LA-1,
Amberlite LA-2,
dibenzylamine,
dioctylamine,
tripentylamine,
triisopentylamine, N,N-dioctylmethylamine,
trihexylamine,
triheptylamine,
trioctylamine and
tridodecylamine.

The reaction of a ketogulonic acid ester of formula I, which can be present also in pyranoid or furanoid form, with an amine is carried out in a suitable organic solvent or in a solvent mixture in which the KGAE and/or the amine used are at least partially soluble. The solvent can be a protic or aprotic dipolar solvent. Examples of protic solvents are lower alcohols containing 1 to 5 carbon atoms such as methanol, ethanol, propanol, isopropanol etc. Examples of aprotic dipolar solvents are acetonitrile, dimethylformamide, dioxan, monoglyme, methyl-cellosolve (ethylene glycol monomethyl ether) etc. The alcohols and especially methanol are preferred solvents. The KGAE's of formula I used as starting materials are known compounds or are analogues of known compounds. They can be used as such in the reaction or can also be prepared previously in situ from 2-ketogulonic acid by esterification with a corresponding alcohol.

The amount of solvent used is, in itself, not critical, but it conveniently lies in a ratio of about 1:1 to about 10:1 (ml/g) based on the KGAE and the amine used.

The amount of amine used in the process provided by the invention conveniently amounts to from about 0.1 to about 1.5, preferably from about 0.5 to about 1.1 and especially from about 0.9 to about 1 mol per mol of ketogulonic acid ester.

The temperature, the pressure and the reaction duration are not critical in the process provided by the invention.

The temperature is the factor determining the velocity. The upper temperature limit is determined by the stability of the reaction partners. The reaction is conveniently carried out at a temperature up to about 90° C., preferably from about 50° C. to about 75° C. and especially at about 65° C.

The pressure at which the process provided by the invention is carried out is not critical and the process can be carried out readily at normal pressure. However, it can under certain circumstances also be carried out under elevated pressure, with correspondingly elevated temperature and correspondingly shorter reaction times.

The reaction time depends on the reaction temperature and, having regard to the optimum temperatures, lies between about 2 to 7 hours and especially between about 3 to 5 hours.

The reaction of the KGAE and the amine can be carried out in the presence or absence of air. It is, however, preferably carried out with the exclusion of air, i.e. under an inert gas such as, for example, nitrogen, argon and the like.

The cleavage of the ascorbic acid amine salt obtained is carried out in accordance with the invention without neutralization, i.e. without addition of an acid or a base. The cleavage as well as the isolation of the pure ascorbic acid and, if desired, of the amine used is carried out by liquid-liquid extraction, whereby the free ascorbic acid passes into the polar phase and the free amine passes into the non-polar phase, or in certain circumstances by simple digestion, i.e. heating with a suitable organic solvent.

Non-polar solvents which are suitable for the extraction are those in which the amine used has a good solubility. An aprotic apolar solvent such as an aliphatic or aromatic hydrocarbon (e.g. hexane, petroleum ether, benzene, toluene, xylene and the like) is conveniently used. Suitable polar solvents or solvent mixtures are those in which the ascorbic acid has a good solubility and which are not miscible with the previously mentioned non-polar solvents. Water, methanol, ethanol, acetonitrile, acetone and the like or mixtures thereof are conveniently used. The presence of at least a small amount of water has been found to be especially convenient. Water or a water-methanol mixture is especially preferred. The temperature at which the extraction is carried out is, in itself, not critical and the extraction can be carried out at room temperature or at an elevated temperature. The extraction is preferably carried out at about room temperature. After the extraction has been carried out, the ascorbic acid as well as the amine used can be isolated readily in a manner known per se from the respective phases containing them.

For the digestion there are suitable in principle the same non-polar solvents as previously mentioned for the extraction. The heating is conveniently carried out at a temperature of about 50° C. up to the reflux temperature of the solvent used. The digestion is preferably carried out at the reflux temperature. The ascorbic acid amine salt is decomposed in this digestion, the pure ascorbic acid precipitating and the amine passing into the organic phase from which it can then be isolated readily in a manner known per se.

All previously mentioned operations can, moreover, be carried out not only continuously but also batchwise.

The following Examples illustrate the present invention in more detail, but are not intended to constitute a limitation:

EXAMPLE 1

26.8 g (128.7 mmol) of ketogulonic acid methyl ester and 125 ml of methanol were added under argon to a 500 ml sulphonation flask provided with a stirrer, thermometer, reflux condenser and 50 ml dropping funnel. Thereupon, the mixture was heated to 65° C. (reflux) while stirring, the ester dissolving. 38 g (109 mol %) of trihexylamine (99.9%) were then added dropwise within 15 minutes from the dropping funnel. Towards the end of the trihexylamine addition the mixture became slightly turbid, but the solution again became clear 5 minutes later. The mixture was now stirred at reflux for a further 4¾ hours, whereby it became yellow in color. After a total of 5 hours, the mixture was rinsed into a 500 ml round flask with methanol and concentrated on a rotary evaporator at 45° C./20 mbar. A yellow viscous oil was obtained as the residue.

The previously obtained oil was dissolved in 50 ml of deionized water and rinsed with about 20 ml of water into a rotary perforator gassed with nitrogen. Thereupon, the mixture was extracted continuously with about 500 ml of n-hexane for 20 hours. The aqueous phase thereby became almost colorless and the organic phase became yellow. After completion of the extraction, the two phases remaining in the extractors were separated in a separating funnel. The organic phases were combined, dried over about 30 g of sodium sulphate and evaporated on a rotary evaporator at 45° C./100-20 mbar. There remained behind 37.8 g of yellow trihexylamine with a content of 97.6%. This corresponded to a yield of trihexylamine of 97.2%.

The aqueous phase which was obtained after the extraction of the trihexylamine contained 21.9 g of ascorbic acid, corresponding to a yield of 96.4%.

EXAMPLE 2

The reaction of ketogulonic acid methyl ester with trihexylamine was carried out in different solvents in an analogous manner to that described in Example 1. The results are compiled in the following Table.

TABLE

| Solvent | Yield of ascorbic acid | Recovered amine |
| --- | --- | --- |
| Ethanol | 92% | 98.6% |
| Isopropanol | 94.1% | 97.9% |
| Methylcellosolve | 93.5% | 97.9% |
| Acetonitrile | 95.8% | 91.3% |

EXAMPLE 3

26.8 g (128.7 mmol) of ketogulonic acid methyl ester and 125 ml of methanol were added under argon to a 500 ml sulphonation flask provided with a stirrer, thermometer and reflux condenser. Thereupon, the mixture was heated to 65° C. (reflux) while stirring, the ester dissolving. 17.5 g (50 mol %) of trihexylamine (99.9%) were then added within 15 minutes. The mixture was stirred at reflux for a further 24 hours, whereby it became yellow in color. The mixture was subsequently rinsed into a 500 ml round flask with methanol and concentrated on a rotary evaporator at 45° C./20 mbar. A yellow viscous oil was obtained as the residue.

The previously obtained oil was dissolved in 50 ml of deionized water and rinsed with about 20 ml of water into a Kutscher-Steudel extractor gassed with nitrogen. Thereupon, the mixture was extracted continuously with about 500 ml of n-hexane for 20 hours. After completion of the extraction, the two phases remaining in the extractor were separated in a separating funnel. The organic phases were combined, dried over about 30 g of sodium sulphate and concentrated on a rotary evaporator at 45° C./100-20 mbar. There remained behind 17.5 g of yellow trihexylamine with a content of 99.0%. This corresponds to a yield of trihexylamine of 99.6%.

The aqueous phase which was obtained after the extraction of the trihexylamine contained 21.2 g of ascorbic acid, corresponding to a yield of 93.5%.

EXAMPLE 4

26.8 g (128.7 mmol) of ketogulonic acid methyl ester and 10 ml of methanol were added under argon to a 100 ml sulphonation flask provided with a stirrer, thermometer, reflux condenser and 50 ml dropping funnel. Thereupon, the mixture was heated to 65° C. (reflux) while stirring. 34.7 g (100 mol %) of trihexylamine (99.9%) were then added dropwise within 15 minutes from the dropping funnel. All passed into solution after approximately 4 hours, but the mixture remained turbid up to the end. The mixture was stirred at reflux for a further 4¾ hours, whereby it became yellow in color. After a total of 5 hours, the mixture was rinsed into a 500 ml round flask with methanol and concentrated on a rotary evaporator at 45° C./20 mbar. A yellow viscous oil was obtained as the residue.

The previously obtained oil was dissolved in 50 ml of deionized water and rinsed with about 20 ml of water into a rotary perforator gassed with nitrogen. Thereupon, the mixture was extracted continuously with about 500 ml of n-hexane for 20 hours. After completion of the extraction, the two phases remaining in the extractor were separated in a separating funnel. The organic phases were combined, dried over about 30 g of sodium sulphate and evaporated on a rotary evaporator at 45° C./100-20 mbar. There remained behind 34.4 g of yellow trihexylamine with a content of 98.3%. This corresponds to yield of trihexylamine of 97.5%.

The aqueous phase which was obtained after the extraction of the trihexylamine contained 21.0 g of ascorbic acid, corresponding to a yield of 92.7%.

EXAMPLE 5

26.8 g (128.7 mmol) of ketogulonic acid methyl ester and 125 ml of methanol were added under argon to a 500 ml sulphonation flask provided with a stirrer, thermometer, reflux condenser and 50 ml dropping funnel. Thereupon the mixture was heated to 65° C. (reflux) while stirring, the ester dissolving. 33.1 g (106.5 mol %) of bis (2-ethylhexyl) amine (100%) were then added during 40 minutes through the dropping funnel while maintaining a pH value of about 6.5. The mixture was subsequently reacted at reflux for a further 3½ hours, whereby it became yellow. The methanol was then distilled off on a rotary evaporator at 45° C./20 mbar. Yellow crystalline ascorbic acid amine salt was obtained.

The previously obtained crystals were suspended in 400 ml of water and 400 ml of n-hexane and the suspension was stirred vigorously for 1 hour, the salt dissolving completely. The aqueous phase was thereupon extracted with two 100 ml portions of n-hexane. The hexane phases were backwashed with two 100 ml portions of water, dried over about 40 g of sodium sulphate and evaporated on a rotary evaporator at 45° C./100-20 mbar. There remained behind 29.2 g (86.5%) of pale yellow bis (2-ethylhexyl) amine with a content of 98%.

The combined aqueous phases were concentrated to about 100 ml and back-extracted continuously in a Kutscher-Steudel extractor for 20 hours with about 300 ml of n-hexane. The organic phase was dried over about 20 g of sodium sulphate and evaporated on a rotary evaporator at 45° C./100-20 mbar. There were thus obtained a further 3.55 g (10.3%) of yellow bis (2-ethylhexyl) amine with a content of 96.1%. This corresponded to a total yield of amine of 96.8%.

The combined aqueous phases which were obtained after the extraction of the amine contain 21.3 g of ascorbic acid, corresponding to a yield of 94.1%.

EXAMPLE 6

26.8 g (128.7 mmol) of ketogulonic acid methyl ester and 25 ml of methanol were added under argon to a 200 ml sulphonation flask provided with a stirrer, thermometer, reflux condenser and 50 ml dropping funnel. Thereupon, the mixture was heated to 65° C. (reflux) while stirring. 29.8 g (100 mol %) of tripentylamine (98.3%) were then added dropwise wthin 15 minutes from the dropping funnel. All passed into solution after approximately 1 hour. The mixture was stirred at reflux for a further 4¾ hours, whereby it became yellow in color. After a total of 5 hours, the mixture was rinsed into a 500 ml round flask with methanol and concentrated on a rotary evaporator at 45° C./20 mbar. A yellow viscous oil was obtained as the residue.

The previously obtained oil was dissolved in 50 ml of deionized water and rinsed with about 20 ml of water into a rotary perforator gassed with nitrogen. Thereupon, the mixture was extracted continuously with about 500 ml of n-hexane for 20 hours. After completion of the extraction, the two phases remaining in the extractor were separated in a separating funnel. The organic phases were combined, dried over about 30 g of sodium sulphate and evaporated on a rotary evaporator at 45° C./100-20 mbar. There remained behind 29.3 g of yellow tripentylamine with a content of 98.7%. This corresponded to a yield of tripentylamine of 98.9%.

The aqueous phase which was obtained after the extraction of the tripentylamine contains 21.9 g of ascorbic acid, corresponding to a yield of 96.5%.

EXAMPLE 7

Different amines were used in an analogous manner to that described in Examples 1 to 6. The results are compiled in the following Table.

TABLE

| Amine | Yield of ascorbic acid | Recovered amine |
|---|---|---|
| Primene JMT | 95.4% | 79.2% |
| α-Amino-diphenylmethane | 90.8% | 66.8% |
| 1.2-Diphenylethylamine | 89.2% | 49.8% |
| Amberlite LA-3[a] | 97.0% | 56.5% |
| Dibenzylamine | 91.9% | 83.3% |
| Dioctylamine | 96.2% | 94.3% |
| Triisopentylamine | 94.3% | 94.9% |
| N,N-Dioctylmethylamine | 92.7% | 91.3% |
| Triheptylamine | 95.8% | 100% |
| Tridodecylamine | 90.4% | 96.1% |
| Amberlite LA-1[a] | 88.3% | 96.5% |
| Amberlite LA-2[a] | 85.6% | 94.3% |

[a]Liquid ion exchanger from Rohm & Haas.

EXAMPLE 8

26.8 g (128.7 mmol) of ketogulonic acid methyl ester and 125 ml of methanol were added under argon to a 500 ml sulphonation flask provided with a stirrer, thermometer, reflux condenser and 100 ml dropping funnel. Thereupon, the mixture was heated to 65° C. (reflux) while stirring, the ester dissolving. 46.2 g (100 mol %) of trioctylamine were then added dropwise within 15 minutes from the dropping funnel. The mixture was now further stirred at reflux for a further 4¾ hours, whereby it became yellow in color. After a total of 5 hours, the mixture was concentrated on a rotary evaporator at 45° C./20 mbar, there remaining behind a viscous two-phase oil.

The previously obtained oil was dissolved in 150 ml of toluene and the solution was heated to reflux temperature while stirring. Upon heating white ascorbic acid began to crystallize fairly rapidly. The mixture was stirred at reflux temperature for a further 1 hour and the precipitate was then filtered off under suction while hot. The residue was washed with 15 ml of toluene and then with 15 ml of hexane and dried overnight at room temperature/20 mbar in a vacuum drying oven. 20.75 g (91.5%) of pure ascorbic acid were obtained.

The filtrate which was obtained after the filtration was evaporated completely on a rotary evaporator and 50.8 g (110%) of crude trioctylamine were obtained.

EXAMPLE 9

26.8 g (128.7 mmol) of ketogulonic acid methyl ester and 125 ml of methanol were added under argon to a 500 ml sulphonation flask provided with a stirrer, thermometer, reflux condenser and 50 ml dropping funnel. Thereupon, the mixture was heated to 65° C. (reflux) while stirring, the ester dissolving. 46.2 g (100 mol %) of trioctylamine (98.3%) were then added dropwise within 15 minutes from the dropping funnel. The mixture was now stirred at reflux for a further 4¾ hours, whereby it became yellow in color. After a total of 5 hours, the mixture was rinsed into a 500 ml round flask with methanol and concentrated on a rotary evaporator at 45° C./20 mbar. A viscous two-phase oil was obtained as the residue.

The previously obtained oil was treated with 150 ml of hexane and heated to reflux temperature (57° C.) while stirring. Yellowish ascorbic acid began to crystallize fairly rapidly. After 1½ hours at reflux, the crystals were filtered off under suction while hot, washed with two 15 ml portions of hexane and dried overnight at room temperature/20 mbar in a vacuum drying oven. There were obtained 23.6 g of ascorbic acid with a content of 90.6%; yield 94.3%.

The filtrate which was obtained after the filtration is evaporated completely on a rotary evaporator and there were obtained 44.8 g of 97.1% trioctylamine. This corresponds to a yield of 95.7%.

EXAMPLE 10

30.4 g (128.7 mmol) of ketogulonic acid isopropyl ester and 125 ml of methanol were added under argon to a 500 ml sulphonation flask provided with a stirrer, thermometer, reflux condenser and 50 ml dropping funnel, the ester dissolving. Thereupon the solution was heated to 65° C. (reflux) while stirring. 34.7 g (100 mol %) of trihexylamine (99.9%) were added dropwise within 15 minutes from the dropping funnel. Towards the end of the trihexylamine addition the mixture became slightly turbid, but the solution again becomes clear 5 minutes later. The mixture was stirred at reflux for a further 6¾ hours, whereby it became yellow in color. After a total of 7 hours, the mixture was rinsed into a 500 ml round flask with methanol and concentrated on a rotary evaporator at 45° C./20 mbar. A yellow viscous oil was obtained as the residue.

The previously obtained oil was dissolved in 50 ml of deionized water and rinsed with about 20 ml of water into a rotary perforator gassed with nitrogen. Thereupon, the mixture was extracted continuously with about 500 ml of n-hexane for 20 hours. After completion of the extraction the two phases remaining in the extractor were separated in a separating funnel. The organic phases were combined, dried over about 30 g of sodium sulphate and evaporated on a rotary evaporator at 45° C./100-20 mbar. There remained behind 36.4 g of yellow trihexylamine with a content of 95.6%. This corresponds to a yield of trihexylamine of 100%.

The aqueous phase which was obtained after the extraction of the trihexylamine contains 16.1 g of ascorbic acid, corresponding to a yield of 70.8%.

EXAMPLE 11

111.1 g of ketogulonic acid ethyl ester (content: 91%) and 100 ml of ethanol were added under argon to a 750 ml sulphonation flask provided with a stirrer, thermometer, reflux condenser and 250 ml dropping funnel. Thereupon the mixture was heated to 65° C. while stirring, the ester dissolving. 134.8 of trihexylamine (99.9%) were then added dropwise within 25 minutes from the dropping funnel. The mixture was stirred at 65° C. for a further 4½ hours, whereby it became red-brown in color. After a total of 5 hours, the mixture was rinsed into a 1000 ml round flask with ethanol and concentrated on a rotary evaporator at 45° C./20 mbar. A brown viscous oil was obtained as the residue.

The previously obtained oil was dissolved in 250 ml of deionized water and the solution was extracted with two 150 ml portions of n-hexane. The hexane phases are backwashed with 50 ml of water, and the combined aqueous phases were back-extracted continuously in a rotary perforator with about 800 ml of n-hexane for 20 hours. After completion of the extraction, the two phases remaining in the extractor were separated in a separating funnel. The organic phases were combined, dried over about 50 g of sodium sulphate and evaporated on a rotary evaporator at 45° C./100-20 mbar. There remained behind 136.7 g of yellow trihexylamine with a content of 98.6%. This corresponded to a yield of trihexylamine of 100%.

The aqueous phase which was obtained after the extraction of the trihexylamine contained 63.1 g of ascorbic acid, corresponding to a yield of 78.5% and 14.8 g of ketogulonic acid ethyl ester, corresponding to a yield of 14.7%.

EXAMPLE 12

The reaction of ketogulonic acid methyl ester with trihexylamine in methanol was carried out in a manner analogous to that described in Example 1, but the extraction was carried out with other solvents. The results are compiled in the following Table:

TABLE

| Extraction solvent | Yield of ascorbic acid | Recovered amine* |
|---|---|---|
| Toluene | 93.9% | 97.4% |
| Petroleum ether | 98.5% | 100.0% |
| Methylcyclohexane | 97.2% | 99.5% |

EXAMPLE 13

26.8 g (128.7 mmol) of ketogulonic acid methyl ester and 125 ml of acetonitrile were added under argon to a 500 ml sulphonation flask provided with a stirrer, thermometer, reflux condenser and 50 ml dropping funnel. Thereupon, the mixture was heated to 78° C. (reflux) while stirring. 34.7 g (100 mol %) of trihexylamine (99.4%) were then added dropwise within 15 minutes from the dropping funnel. The ester passed into solution completely after a reaction period of about 1 hour. After stirring for a total of 2½ hours at reflux temperature, the orange-brown mixture was added to a rotary perforator gassed with nitrogen. Thereupon, the mixture was extracted continuously with about 500 ml of n-hexane for 20 hours. 1 hour after the beginning of the extraction, ascorbic acid crystallizes out slowly from the acetonitrile phase. After completion of the extraction, the content of the extractor was suction filtered. The yellowish crystals were washed with hexane and acetonitrile and dried overnight in a desiccator. There were obtained 20.6 g of ascorbic acid with a content of 99.5%, corresponding to a yield of 90.4%.

The mother liquor which was obtained after the filtration was separated in a separating funnel. The two hexane phases were combined, dried over about 30 g of sodium sulphate and evaporated on a rotary evaporator at 45° C./100-20 mbar. There remained 34.9 g of yellow trihexylamine with a content of 98.2%. This corresponds to a yield of trihexylamine of 99.4%.

The orange acetonitrile phase contained a further 0.8 g of ascorbic acid. Together with the crystallized ascorbic acid, this corresponds to a yield of 93.7%.

We claim:

1. A process for producing ascorbic acid comprising the steps of:
    a) reacting a ketogulonic acid ester having the formula

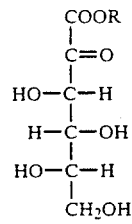

wherein R is lower alkyl with an amine containing 12 to 38 carbon atoms selected from the group consisting of straight chain or branched chain primary amines, straight chain or branched chain secondary amines, and straight chain or partially branched chain aliphatic tertiary amines, in a protic or aprotic dipolar solvent to form an ascorbic acid amine salt having the formula

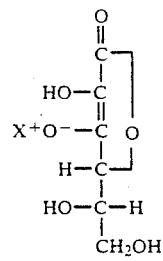

wherein X is the ammonium ion of the amine used, and
    b) cleaving the resulting ascorbic acid amine salt by liquid-liquid extraction such that the ascorbic acid is recovered in the polar phase and the amine used is recovered in the non-polar phase.

2. A process according to claim 1, wherein a straight-chain tertiary alkylamine containing 15 to 30 carbon atoms is used as the amine.

3. A process according to claim 1, wherein a branched-chain secondary alkylamine containing 16 to 25 carbon atoms is used as the amine.

4. A process according to claim 1, wherein a branched-chain primary alkylamine containing 12 to 24 carbon atoms is used as the amine.

5. A process according to claim 2, wherein said tertiary alkylamine is tripentylamine, triisopentylamine, N,N-dioctylmethylamine, trihexylamine, triheptylamine, trioctylamine or tridodecylamine.

6. A process according to claim 3, wherein said secondary alkylamine is selected from bis (2-ethylhexyl) amine, dioctylamine, Amberlite LA-1 or Amberlite LA-2.

7. A process according to claim 4 wherein said branched chain amine is selected from Primene JMT or Amberlite LA-3.

8. A process according to claim 1, wherein a lower alcohol containing 1 to 5 carbon atoms is used as the organic solvent.

9. A process according to claim 1, wherein the amine is used in an amount of about 0.1 to about 1.5 mol per mol of ketogulonic acid ester.

10. A process according to claim 1, wherein the reaction of the ketogulonic acid ester with the amine is carried out at a temperature up to about 90° C.

* * * * *

UNITED STATES PATENT AND TRADEMARK OFFICE
CERTIFICATE OF CORRECTION

PATENT NO. : 5,041,563

DATED : August 20, 1991

INVENTOR(S) : PETER FAHRNI AND THEODOR SIEGFRIED

It is certified that error appears in the above-identified patent and that said Letters Patent is hereby corrected as shown below:

Claim 7, column 10, line 58, between "chain" and "amine" insert -- primary --.

Signed and Sealed this

Twenty-fourth Day of November, 1992

Attest:

DOUGLAS B. COMER

Attesting Officer — Acting Commissioner of Patents and Trademarks